United States Patent
Kim et al.

(10) Patent No.: US 9,594,055 B2
(45) Date of Patent: Mar. 14, 2017

(54) SENSING APPARATUS USING A RADIO FREQUENCY SIGNAL, AND MANUFACTURING METHOD THEREOF

(71) Applicants: SAMSUNG ELECTRONICS CO., LTD., Suwon-si (KR); INDUSTRY-ACADEMIC COOPERATION FOUNDATION, YONSEI UNIVERSITY, Seoul (KR)

(72) Inventors: Duck Hwan Kim, Goyang-si (KR); Seong Chan Jun, Seoul (KR); Chul Soo Kim, Hwaseong-si (KR); In Sang Song, Osan-si (KR); Jea Shik Shin, Hwaseong-si (KR)

(73) Assignees: Samsung Electronics Co., Ltd., Suwon-si (KR); Industry-Academic Cooperation Foundation, Yonsei University, Seoul (KR)

( * ) Notice: Subject to any disclaimer, the term of this patent is extended or adjusted under 35 U.S.C. 154(b) by 212 days.

(21) Appl. No.: 13/787,940

(22) Filed: Mar. 7, 2013

(65) Prior Publication Data

US 2013/0248368 A1 Sep. 26, 2013

(30) Foreign Application Priority Data

Mar. 23, 2012 (KR) .................. 10-2012-0030096

(51) Int. Cl.
*G01N 27/447* (2006.01)
*B03C 5/00* (2006.01)
*B03C 5/02* (2006.01)

(52) U.S. Cl.
CPC ....... *G01N 27/44791* (2013.01); *B03C 5/005* (2013.01); *B03C 5/026* (2013.01); *B03C 2201/26* (2013.01); *Y10T 156/10* (2015.01)

(58) Field of Classification Search
CPC ...... C12N 11/14; G01N 27/447; G01N 27/26; Y10T 156/10; B03C 2201/26
See application file for complete search history.

(56) References Cited

U.S. PATENT DOCUMENTS

| 7,927,978 B2 | 4/2011 | Pfeiffer |
| 2002/0029979 A1* | 3/2002 | Freund .................. G01N 21/78 205/775 |

(Continued)

FOREIGN PATENT DOCUMENTS

| JP | 2009-244188 | 10/2009 |
| JP | 2010-230369 | 10/2010 |

(Continued)

*Primary Examiner* — Jennifer Dieterle
(74) *Attorney, Agent, or Firm* — NSIP Law (57) ABSTRACT

A sensing apparatus using a radio frequency and a manufacturing method thereof is provided. A sensing apparatus using a radio frequency includes a protecting layer configured to protect a substrate from migration of electrons occurring as the radio frequency is applied to a first electrode and a second electrode, a channel forming layer configured to form a channel based on a field between the first electrode and the second electrode, the channel forming layer using a polarized carbon-based nano material to form the channel, and a sensing layer configured to sense glucose using a medium material that is attached on the carbon-based nano material.

10 Claims, 6 Drawing Sheets (56) References Cited

U.S. PATENT DOCUMENTS

| | | | |
|---|---|---|---|
| 2009/0084678 A1* | 4/2009 | Joshi et al. | 204/403.14 |
| 2010/0089774 A1* | 4/2010 | Manohar et al. | 205/792 |
| 2012/0134880 A1* | 5/2012 | Kurkina et al. | 422/82.01 |
| 2013/0130513 A1* | 5/2013 | Miyatani et al. | 438/782 |

FOREIGN PATENT DOCUMENTS

| | | | |
|---|---|---|---|
| JP | 2010-230379 | | 10/2010 |
| KR | 10-2008-0005303 | | 1/2008 |
| KR | 10-2009-0124330 | | 12/2009 |
| KR | 10-2010-0001062 | | 1/2010 |
| KR | 10-2010-0022165 | | 3/2010 |
| KR | 10-2010-0081786 | | 7/2010 |
| WO | WO/2012/011480 | * | 1/2012 |

* cited by examiner

SENSING APPARATUS USING A RADIO FREQUENCY SIGNAL, AND MANUFACTURING METHOD THEREOF

CROSS-REFERENCE TO RELATED APPLICATIONS

This application claims the benefit under 35 U.S.C. §119 (a) of Korean Patent Application No. 10-2012-0030096, filed on Mar. 23, 2012, in the Korean Intellectual Property Office, the entire disclosure of which is incorporated herein by reference for all purposes.

BACKGROUND

1. Field

The following description relates to a sensing apparatus using a radio frequency and a manufacturing method thereof.

2. Description of Related Art

Results of glucose measurement generally depend on sensitivity of a certain parameter. Generally, to measure an amount of glucose, glucose sensors employ electrochemistry and a light emitting material.

SUMMARY

In one general aspect, there is provided a sensing apparatus using a radio frequency, the apparatus including a protecting layer configured to protect a substrate from migration of electrons occurring as the radio frequency is applied to a first electrode and a second electrode, a channel forming layer configured to form a channel based on a field between the first electrode and the second electrode, the channel forming layer using a polarized carbon-based nano material to form the channel, and a sensing layer configured to sense glucose using a medium material that is attached on the carbon-based nano material.

The apparatus may further include that the protecting layer is on the substrate and includes a high-resistance silicon oxide based material.

The apparatus may further include that the polarized carbon-based nano material is polarized along a direction of the field.

The apparatus may further include that, when the field is formed by applying direct current (DC) voltage or alternating current (AC) voltage to the first electrode and the second electrode, the channel forming layer is further configured to form the channel based on a dielectric phoresis scheme.

The apparatus may further include that the polarized carbon-based nano material is configured to migrate toward the field using a dipole moment in the channel forming layer such that the channel is formed.

The apparatus may further include that the polarized carbon-based nano material includes one or more layers of graphene or a carbon nano tube (CNT).

The apparatus may further include that the glucose is bonded by an oxidant to the medium material for at least a predetermined period, and the sensing layer is configured to sense a concentration of the glucose.

The apparatus may further include that the medium material includes poly aminophenyl boronic acid.

The apparatus may further include a hexagonal-boron nitride (h-BN) layer between the channel forming layer and the protecting layer, the h-BN layer being configured to decrease a dielectric loss of electrons within a range of the applied radio frequency.

In another general aspect, there is provided a sensing apparatus using a radio frequency, the apparatus including a sensing unit configured to sense a concentration of glucose that reacts with a medium material attached on a carbon-based nano material, the sensed concentration of glucose being based on an electrical characteristic value that is measured in a first electrode and a second electrode, and a control unit configured to control a radio frequency signal that is applied to the first electrode and the second electrode.

The apparatus may further include that the electric characteristic value includes S-parameter and resistance R, inductance L, conductance G, and capacitance C (RLGC) values.

The apparatus may further include that the sensing unit includes a channel forming unit and a measuring unit, the channel forming unit being configured to form a channel using a polarized carbon-based nano material, based on a field that is formed between the first electrode and the second electrode, the measuring unit being configured to measure an S-parameter, a resistance, an inductance, a conductance, and a capacitance in the first electrode and the second electrode, based on flow of electrons that migrate via the formed channel.

The apparatus may further include that the carbon-based nano material includes one or more layers of graphene or a carbon nano tube (CNT).

The apparatus may further include that the medium material includes poly aminophenyl boronic acid.

The apparatus may further include that the first electrode and the second electrode are ground-signal-ground (GSG) electrodes.

In yet another general aspect, there is provided a manufacturing method of a sensing apparatus using a radio frequency, the method including disposing a protecting layer on a substrate, the protecting layer being configured to protect the substrate from migration of electrons occurring as the radio frequency is applied to a first electrode and a second electrode, attaching a hexagonal-boron nitride (h-BN) layer on the protecting layer via an adhesive tape, disposing a carbon-based nano material on the h-BN layer and between the first electrode and the second electrode, the carbon-based nano material being configured to use a field that is formed between the first electrode and the second electrode, and attaching a medium material on the carbon-based nano material.

The method may further include that the carbon-based nano material includes one or more layers of graphene or a carbon nano tube (CNT).

The method may further include that the medium material includes poly aminophenyl boronic acid.

Other features and aspects will be apparent from the following detailed description, the drawings, and the claims.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, description of well-known functions and constructions may be omitted for increased clarity and conciseness.

Figure 1:
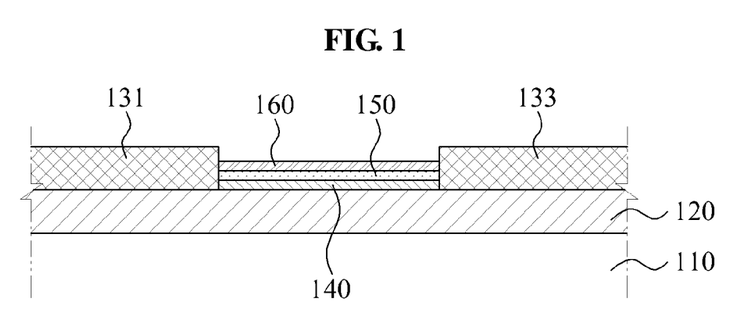
FIG. 1 is a cross-sectional view illustrating an example of a sensing apparatus using a radio frequency.

FIG. 1 is a cross-sectional view illustrating an example of a sensing apparatus using a radio frequency. Referring to the example illustrated in FIG. 1, the sensing apparatus using the radio frequency includes a substrate 110, a protecting layer 120, a first electrode 131, a second electrode 133, a hexagonal-boron nitride (h-BN) layer 140, a channel forming layer 150, and a sensing layer 160.

In an example, the protecting layer 120 protects the substrate 110 from migration of electrons as the radio frequency is applied to the first electrode 131 and the second electrode 133. In another example, when an alternating current (AC) signal or a direct current (DC) signal is applied to the first electrode 131 and the second electrode 133, a channel is formed through the channel forming layer 150. In yet another example, the protecting layer 120 prevents electrons that are migrating through the channel from migrating to the substrate 110.

The protecting layer 120 is disposed on the substrate 110. In an example, the protecting layer 120 is formed of a high-resistance silicon oxide based material.

In an example, the channel forming layer 150 forms a channel using a polarized carbon-based nano material based on a field that is formed between the first electrode 131 and the second electrode 133. In another example, when voltage is applied to the first electrode 131 and the second electrode 133, an electric field is formed. In yet another example, the carbon-based nano material is disposed on the protecting layer 120 and between the first electrode 131 and the second electrode 133.

In an example, when an electric field is formed between the first electrode 131 and the second electrode 133, the carbon-based nano material is polarized along the direction of the electric field. In another example, the carbon-based nano material includes graphene. In yet another example, polarized graphene forms a channel through which electrons migrate. In a further example, a polarized carbon-based nano material includes one or more layers of graphene or a carbon nano tube (CNT).

In an example, when an electric field is formed between the first electrode 131 and the second electrode 133 by applying DC voltage or AC voltage to the first electrode 131 and the second electrode 133, the channel forming layer 150 forms a channel based on a dielectric phoresis scheme. In this example, the polarized carbon-based nano material migrates towards the electric field using a dipole moment in the channel forming layer 150. In a further example, the polarized carbon-based nano material is gathered between the first electrode 131 and the second electrode 133 and is gradually and increasingly bonded thereto by van der Waals forces occurring due to pi-stacking. In an additional example, the channel is formed because of the above-referenced bonding.

In an example, the sensing layer 160 senses glucose using a medium material that is attached on the carbon-based nano material. In another example, the sensing layer senses a concentration of glucose that is bonded by an oxidant to the medium material for at least a predetermined period. In this example, the predetermined period indicates a minimum amount of time needed to sense a concentration of glucose. In an additional example, the medium material and glucose are permanently bonded to each other using the oxidant. In a further example, when the oxidant is added in aqueous solution including glucose, glucose and the medium material react irreversibly.

In an example, when a small amount of blood is positioned on the sensing layer 160, the glucose contained in the blood reacts with the medium material. In another example, since the sensing layer 160 senses a concentration of glucose contained in the blood, the sensing apparatus using the radio frequency is used to measure a blood glucose level.

In an example, the medium material includes poly aminophenyl boronic acid, such as 3-aminophenyl boronic acid. An h-BN layer 140 is disposed between the channel forming layer 150 and the protecting layer 120 to decrease dielectric loss of electrons within the range of the applied radio frequency.

Figure 2:
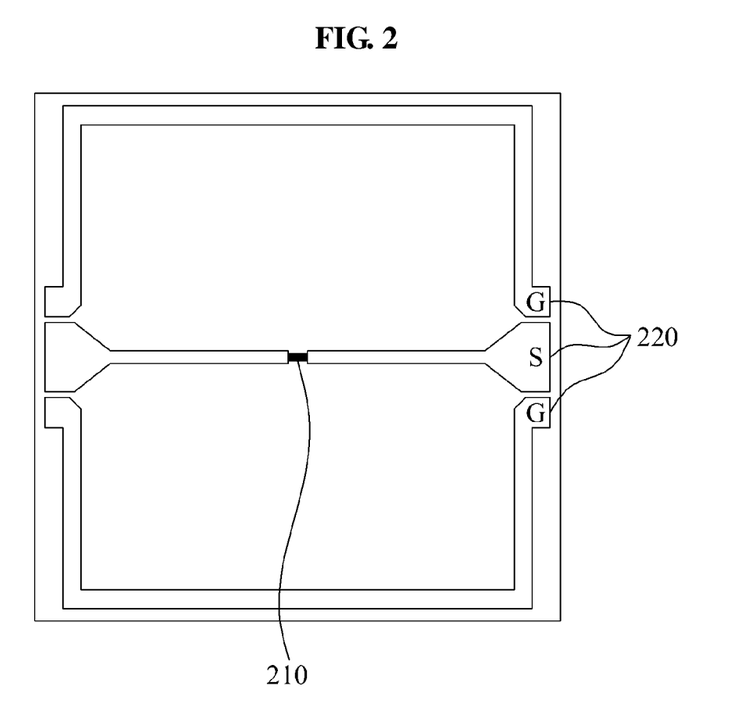
FIG. 2 is a top view illustrating an example of a sensing apparatus using a radio frequency.

FIG. 2 is a top view illustrating an example of a sensing apparatus using a radio frequency. Referring to the example illustrated in FIG. 2, an electrode of the sensing apparatus using the radio frequency may be formed in a structure of a ground-signal-ground (GSG) electrode 220. The GSG electrode 220 is an electrode structure in which both sides of a signal electrode are grounded. A carbon-based nano material 210 is disposed between signal electrodes. In an example, the sensing apparatus using the radio frequency senses a concentration of glucose by bonding glucose and a medium material attached on the carbon-based nano material 210. FIG. 2 illustrates an example of the sensing apparatus using the radio frequency that is expressed based on a chip unit.

Figure 3:
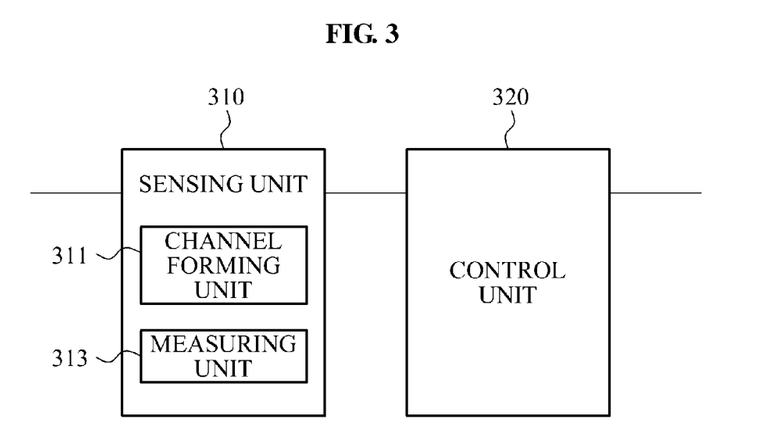
FIG. 3 is a block diagram illustrating an example of a sensing apparatus using a radio frequency.

FIG. 3 is a block diagram illustrating an example of a sensing apparatus using a radio frequency. Referring to the example illustrated in FIG. 3, the sensing apparatus using the radio frequency includes a sensing unit 310 and a control unit 320.

In an example, the sensing unit 310 senses a concentration of glucose that reacts with a medium material attached on a carbon-based nano material, based on an electrical characteristic value that is measured in a first electrode and a second electrode. In this example, the electrical characteristic value includes S-parameter and resistance R, inductance L, conductance G, and capacitance C (RLGC) values. For example, in an S-parameter, transmissivity and reflectivity may be measured. In another example, the sensing unit 310 senses a concentration of glucose based on S-parameter and RLGC values, which have different values based on a concentration of glucose.

In an example, the control unit 320 controls a radio frequency signal to be applied to the first electrode and the second electrode. The electrical characteristic value may be differently measured based on the radio frequency value that is applied to the first electrode and the second electrode. In an example, the control unit 320 determines a signal to be applied within a frequency domain from 0.5 MHz to 4.5 GHz.

The sensing unit 310 includes a channel forming unit 311 and a measuring unit 313. In an example, the channel forming unit 311 forms a channel using a polarized carbon-based nano material, based on a field that is formed between the first electrode and the second electrode. In another example, the channel is formed by overlapping the carbon-based nano material polarized towards the field. In a further example, the measuring unit 313 measures the S-parameter and resistance, inductance, conductance, and capacitance in the first electrode and the second electrode, based on a flow of electrons that migrate via the channel.

In an example, the carbon-based nano material includes one or more layers of graphene or a CNT. In another example, the medium material includes poly aminophenyl boronic acid, such as 3-aminophenyl boronic acid. In a further example, the first electrode and the second electrode are formed in a structure of a GSG electrode.

Figure 4:
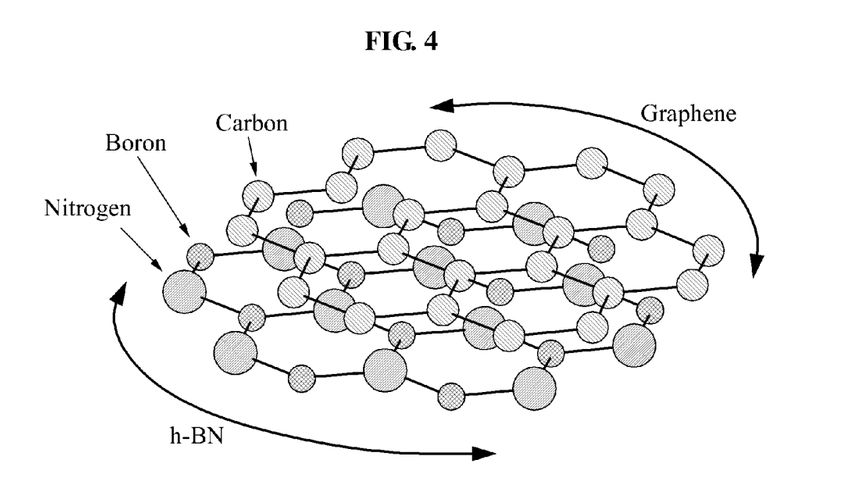
FIG. 4 is a view illustrating an example of a chemical structure of hexagonal-boron nitride (h-BN) used in a sensing apparatus using a radio frequency.

FIG. 4 is a view illustrating an example of a chemical structure of h-BN used in a sensing apparatus using a radio frequency. Boron nitride uses a chemical symbol of BN. Boron and nitride have the same number of electrons as the number of electrons included in a lattice structure including carbon. h-BN is formed in a hexagonal atomic structure similar to graphite and has a very stable and flexible property among allotropes of BN.

BN does not exist in a natural state and, thus, in an example, is generated by synthesizing boric acid and boron trioxide. For example, even though initial BN has a non-crystal form, h-BN has a crystal form and, thus, may have beneficial properties in electrical characteristics, such as mobility and other properties known to one of ordinary skill in the art.

In an example, a semiconductor device including silicone and silicon oxide is used to form a nano or micro-sized sensor structure. In a further example, h-BN is attached on the silicon oxide of the semiconductor device using adhesive tape, and, thus, is formed to have a desired shape because of etching.

Figure 5:
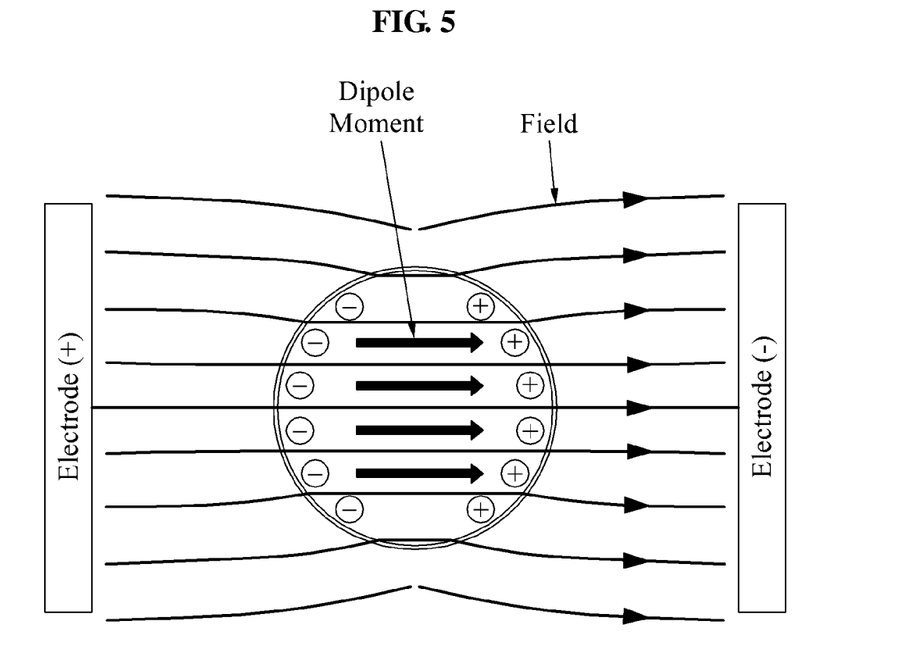
FIG. 5 is a diagram illustrating an example of a dielectric phoresis (DEP) scheme used to form a channel by a sensing apparatus using a radio frequency.

FIG. 5 is a diagram illustrating an example of a dielectric phoresis (DEP) scheme used to form a channel by a sensing apparatus using a radio frequency. Referring to the example illustrated in FIG. 5, graphene is used to form a channel between two electrodes. Graphene has a structure in which a nano-sized carbon atom is present in a hexagonal form on a two-dimensional (2D) plane. A single layer of graphene has a thickness of about 0.4 nm, which is equal to a diameter of the carbon atom. Graphene is usable in an aqueous solution state by generating a solvent in a suspension form.

In an example, carbon uses four electrons in the case of a covalent bond. In another example, $C_{12}$, $C_{13}$, and $C_{14}$ are naturally generated as allotropes of carbon. While $C_{12}$ and $C_{13}$ are stable, $C_{14}$ is a reflective material having a half-life of about 5730 years. Graphite, diamond, amorphous carbon, and other similar materials known to one of ordinary skill in the art are generally known as materials including carbon. Shapes of all the allotropes are generally in a solid state. In a thermal aspect, graphite is most stable.

In an example, a DEP scheme is employed as a method to form a channel using graphene. In an example of employing the DEP scheme, when AC voltage or DC voltage is applied to two electrodes, an electric field may be formed between the two electrodes. As an example result, graphene is polarized due to the electric field. In an example of this polarized state, graphene particles generate force from negative ions to positive ions. An example of such force triggers a dipole moment and enables graphene particles to move toward the electric field. Accordingly, in an example, graphene particles are gathered between the electrodes towards the electric field and van der Waals forces occur due to pi-stacking. Through the van der Waals forces of an example, graphene is bonded to each other, thereby forming a channel.

In an example, the van der Waals forces occur due to attractive forces acting between two molecules. When two molecules are close to each other, a repulsive force is present between electrons of the respective molecules. Thus, motion of electrons occurs in different portions of the molecules. In this instance, the attractive force acts between an electron of one molecule and a portion of another molecule having a positive charge, whereby the two molecules have a mutually attracting force and, in an example, are attached to each other.

Figure 6:
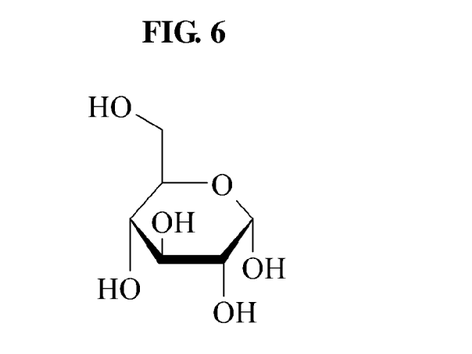
FIG. 6 is a view illustrating an example of a chemical structure of glucose to be sensed by a sensing apparatus using a radio frequency.

FIG. 6 is a view illustrating an example of a chemical structure of glucose to be sensed by a sensing apparatus using a radio frequency. Phosphate buffered saline (PBS) is aqueous solution that is generally used in the bionics field and indicates saline solution that includes, in water, sodium chloride, sodium phosphate, potassium chloride, potassium phosphate, and other compounds known to one of ordinary skill in the art. The saline solution constantly maintains PH and has the same condition as the inside of a human body.

In glucose ($C_6H_{12}O_6$), five carbons and one oxygen constitute a ring structure, five hydroxides are bonded to five carbons, a remaining carbon is unit-bonded to another carbon, and one hydroxide is bonded to the unit-bonded carbon.

Figure 7:
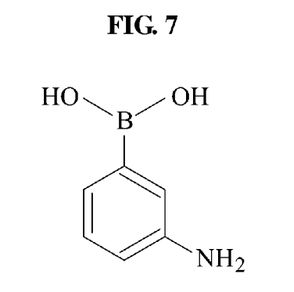
FIG. 7 is a view illustrating an example of a chemical structure of a 3-aminophenyl boronic acid used as a medium material by a sensing apparatus using a radio frequency.

FIG. 7 is a view illustrating an example of a chemical structure of a 3-aminophenyl boronic acid used as a medium material by a sensing apparatus using a radio frequency. In an example, poly aminophenyl boronic acid (PBA), such as, 3-aminophenyl boronic acid, is used as a medium material to sense glucose. As illustrated in the example of FIG. 7, one side of this material is provided in an aromatic ring structure. The aromatic ring structure has a single amine group. The aromatic structure enables mutual pi-stacking. Thus, in an example, PBA is attached on the surface of graphene using the van der Waals forces and forms a functional group capable of sensing glucose.

Another side of PBA includes boronic acid and includes boron and diol. Diol includes two hydroxides. On the other side of PBA, diol is bonded to glucose. PBA has five outermost electrons, shares two electrons with diol, shares a single electron with carbon in the aromatic ring structure, and, thereby, has a single pair of unshared electrons.

An equilibrium constant denotes a concentration relationship where a chemical reaction between a reactant and a product forms equilibrium at a predetermined temperature. A pressure and a concentration do not affect the equilibrium constant. The equilibrium constant has a predetermined constant value at all times regardless of initial concentrations of the reactant and the product. In an example, the relationship equation of the equilibrium constant is as shown in Equation 1.

$$K_C = \frac{[S]^\sigma [T]^\tau}{[A]^\alpha [B]^\beta} \qquad \text{Equation 1}$$

A and B are positioned in the denominator as concentrations of reactants, and S and D are positioned in the numerator as concentrations of products. When a value of $K_c$ increases, values of S and T increase, and thereby indicate that a forward reaction is actively occurring and a ratio of products is great compared to a ratio of reactants. When a reactant is vapor, a partial pressure of atmosphere is used instead of a concentration, and the equilibrium constant is expressed as $K_p$.

A radio frequency refers to the frequency range from 3 KHz to 300 GHz and generally refers to a frequency of an electrical signal rather than a frequency of mechanical vibration. In the above frequency range, current tends to flow on the surface of a conductor rather than flow through the conductor. Such tendency is referred to as the skin effect.

In a relatively low frequency range, current tends to flow through a conductor. Accordingly, in an example including a high frequency, electrons pass through a material such as a dielectric present between capacitors. In another example including the high frequency, loss of electrons occurs. In this example, an electron that passes through a dielectric and thereby gets lost is referred to with respect to a dielectric loss factor, which is a unit that generally uses Siemens and indicates an inverse number of resistance.

Figure 8:
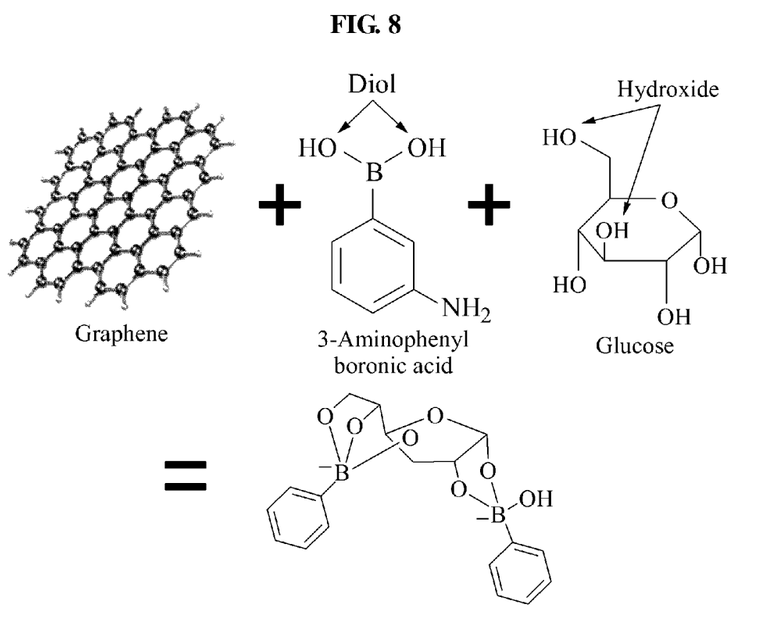
FIG. 8 is a view illustrating an example of a process of bonding graphene, a medium material, and glucose by a sensing apparatus using a radio frequency.

FIG. 8 is a view illustrating an example of a process of bonding graphene, a medium material, and glucose by a sensing apparatus using a radio frequency.

In an example, a medium material and glucose are reversibly chemically bonded to each other in an aqueous solution state, and a bonding level is thereby determined based on the equilibrium constant. The reversible reaction between glucose and the medium material is converted to be irreversible by applying an appropriate chemical reaction to the above conditions. Through the above-referenced chemical reaction, two materials are permanently bonded to each other.

In addition, the medium material between glucose and graphene is a biocompatible material, and is suitable to transfer an electrical signal through being bonded to glucose and graphene.

In an example, to reduce a dielectric loss of electrons in the radio frequency range, h-BN is used as a high resistance material between graphene and silicon oxide. In another example, a limit of a sensitivity of a sensor is determined by measuring a minimum value of an electrical characteristic.

In an example, a change in a measured signal according to a concentration of glucose is used to measure a concentration of glucose. A variety of methods has been developed to measure a concentration of glucose, such as, for example, an electrochemical method and a method of using a light emitting material.

The electrochemical method uses an oxidation-reduction reaction. Glucose oxidase triggers the oxidation-reduction reaction of glucose. In an example, oxygen dissolved in water and a medium known to one of ordinary skill in the art to enable an electron occurring in glucose to effectively reach an electrode is used. Accordingly, in another example, in addition to glucose, various materials are additionally used to determine a concentration of glucose.

The method of using a light emitting material is performed according to a phenomenon providing that a light emitting level decreases in a chemical bond with glucose by attaching a light emitting material. As a result, in an example, this method determines a concentration of glucose by determining a wavelength and intensity of light. A light emitting material and glucose are in electrolyte and aqueous solution. As a result, in another example, a wavelength with respect to an actual light emission and a wavelength obtained by measuring scattering of light in electrolyte vary due to scattering or the effect of an obstacle during a light emission process.

In an example, a sensing apparatus using a radio frequency in a sensor employs an electrical measurement value that is obtained through a covalent bond of glucose. A variety of materials is not needed. In addition, the sensor is present in the air and forms a channel for migration of electrons. As a result, the sensor measures an electrical signal.

In an example, graphene is generated by generating graphene in a form of particles using a hummer method and dissolving the particles in a predetermined solvent. In another example, graphene in a form of particles is present in a suspension state on an electrode that is formed using a photo lithography technology, and is positioned between electrodes and on h-BN along an electric field.

When a channel is formed, in an example, a biocompatible functional group is used for a bond with glucose. In another example, PBA is used as a material that is biocompatible, bonded to glucose, and attached on graphene, thereby enabling transfer of an electrical signal.

In an example, PBA is attached on graphene using van der Waals forces. In another example, a bond through van der Waals forces is weak compared to a covalent bond, but is a strong bond that cannot be easily broken. In a further example, PBA and graphene exchange an electrical signal.

When glucose solution is dropped on a sensor formed with the functional group, in an example, glucose is covalently bonded to the functional group. Another end of the functional group includes boronic acid, and includes diol that includes two borons and two hydroxides. Hydroxide is OH− in aqueous solution and, thus, cannot be bonded to another OH− due to a repulsive force. However, in another example, hydroxide is chemically bonded to boron and loses charge of a negative ion, thereby being in a neutral state. In a further example, boron is bonded to a saccharride structure.

When glucose is bonded to PBA, in an example, a bonding structure of 1:2 is formed by combining two moles of PBA and one mole of glucose. In another example, single PBA may form $H_2O$ by being bonded to two hydroxides of glucose and be bonded thereto. In a further example, single PBA is bonded to two hydroxides of glucose to thereby form $H_2O$ and be bonded thereto. Accordingly, in an example when glucose solution is applied to PBA by dissolving glucose into PBS, $H_2O$ generates in aqueous solution. In an additional example, the generated $H_2O$ is present as H+ and OH−.

Figure 9:
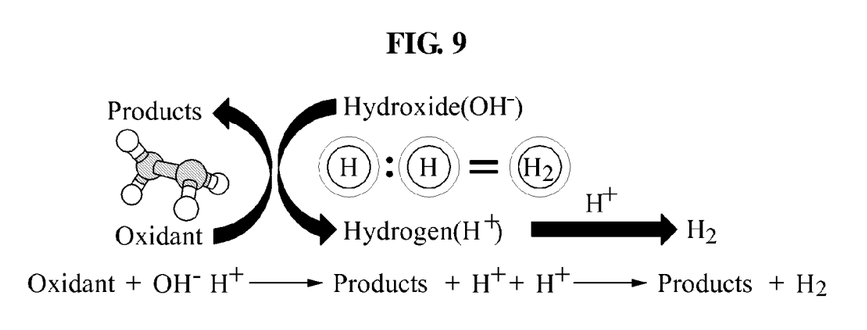
FIG. 9 is a view illustrating an example of a process of producing a non-aqueous solvent using an oxidant by a sensing apparatus using a radio frequency.

FIG. 9 is a view illustrating an example of a process of producing a non-aqueous solvent using an oxidant by a sensing apparatus using a radio frequency.

When removing aqueous solution after bonding glucose and PBA in solution, in an example, the bounded glucose and PBA are separated from each other through a reversible process based on an equilibrium constant condition.

Regardless of pressure and concentration, a bond of glucose and PBA has a predetermined equilibrium constant in a predetermined temperature. In an example, H+ and OH− of $H_2O$ are reversely bonded to diol and hydroxide and thereby return to glucose and PBA that are initial reactants.

In an example, a method of permanently bonding glucose and PBA transforms a solvent. In the case of aqueous solution, a solvent has an aqueous property and, thus, in another example, H+ and OH− are present in the solvent. By transforming the solvent to a non-aqueous material, it is possible to remove components of H+ and OH−, and to permanently covalently bond glucose and PBA.

In an example, an oxidant is used to change a property of solvent. When an oxidant in a liquid form is placed in a material having an aqueous property, in another example, the material having the aqueous property and the liquid oxidant are present in a mixed state in a solvent portion of the aqueous solution. In this example, the oxidant is present in reduced liquid while removing oxide of OH−, and hydrogen of OH− is covalently bonded to remaining H+, thereby being in a vapor state and removed in order to maintain a stable state.

When the aqueous property is completely removed using the oxidant, in an example, the bonded glucose and PBA are in a completely covalently bonded state. When a reverse reaction is triggered due to equilibrium constant, in another example, glucose and PBA are in an ion state and, thus, cannot return to the respective molecular forms by cutting the bond.

Figure 10:
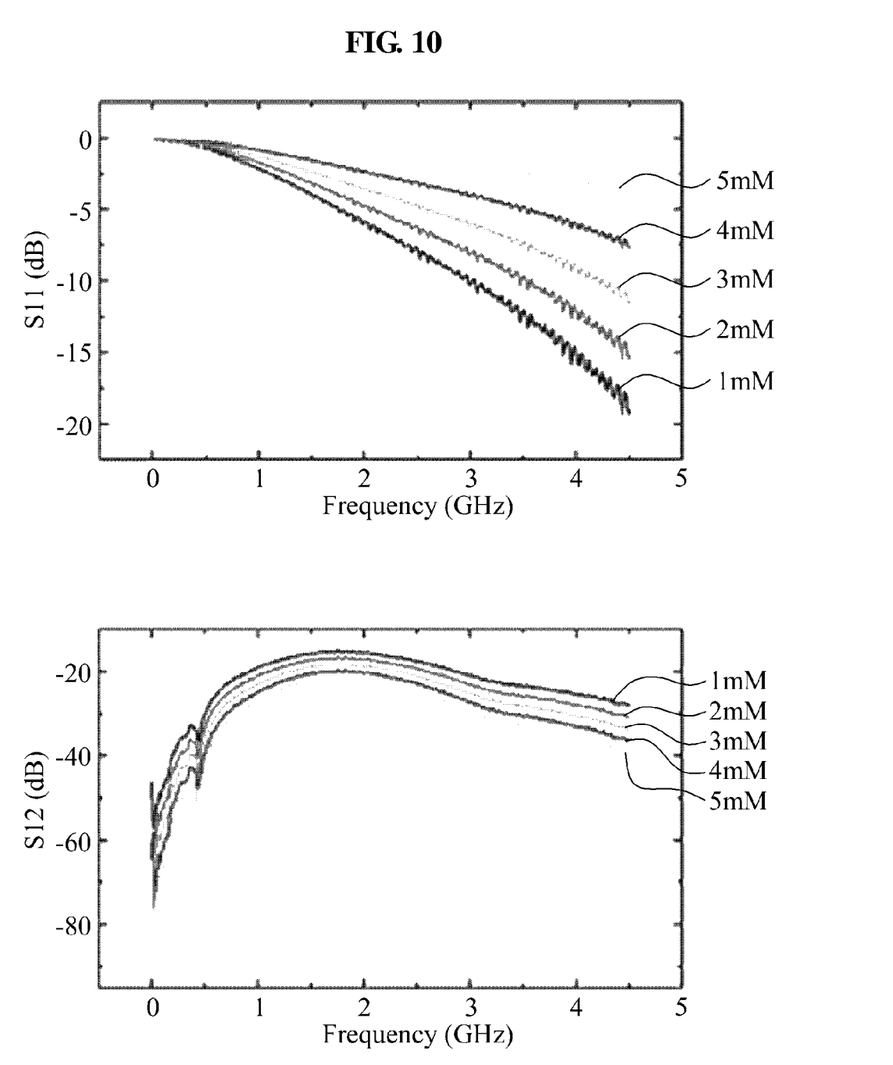
FIG. 10 is a plurality of graphs illustrating examples of an S-parameter measured by a sensing apparatus using a radio frequency.

FIG. 10 is a plurality of graphs illustrating examples of an S-parameter measured by a sensing apparatus using a radio frequency.

Data of S11 and S12 was obtained because of a measuring of an S-parameter. S11 corresponds to an amount of electrons that are reflected and returned to an electrode when electrons migrate between two signal electrodes through a channel, and S12 denotes an amount of electrons that migrate through a channel, thereby moving to an opposite electrode.

In a high frequency domain, when an electron migrates through a channel, in an example. an electron passes through a dielectric and is thereby conducted to silicone that is a conductor. In this example, silicone having a high resistance is used to minimize an amount of penetration.

According to an example, a sensing apparatus using a radio frequency permanently bonds glucose onto PBA and, subsequently, measures a concentration of glucose based on S-parameter and RLGC values that are obtained from an electrical signal of a high frequency.

In an example, measurement values of five factors are used by adding four factors, RLGC, to S parameter. In another example, a numerical value and a peak value according to a concentration of glucose are measured in R indicating resistance and L indicating inductance.

In the case of a glucose component, according to a higher frequency, a sensitive electrical signal appears with respect to a target material. Therefore, in an example, a detection value is obtained and measurement is performed based on a millimole unit.

In an S-parameter obtained by measuring a concentration of glucose, an upper graph of FIG. 10 shows S11 and a lower graph of FIG. 10 shows S12. In the upper graph of FIG. 10, a numerical value increases according to an increase in a concentration of glucose. The lower graph of FIG. 10 shows an opposite shape to the upper graph of FIG. 10. That is, it is possible to measure the tendency of S12 and S11 based on a concentration of glucose. Conversely, it is possible to measure a concentration of glucose based on measurement values and tendency of S12 and S11.

By directly sensing glucose using a radio frequency signal applied to an electrode, it is possible to measure a concentration of glucose without using an additional material to increase the sensing sensitivity of glucose.

By sensing glucose in a saccharride structure using poly aminophenyl boronic acid and graphene between electrodes, it is possible to produce an apparatus capable of sensing glucose.

Since a sensor is structurally miniaturized, it is possible to embed the sensor in various portable devices so that a user is able perform a self-diagnosis of a sugar value without being restricted as to place or occasion.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A sensing apparatus configured to use a radio frequency signal to perform sensing, the apparatus comprising:
 a protecting layer configured to protect a substrate from a migration of electrons occurring as the radio frequency signal is applied to a first electrode and a second electrode;
 a channel forming layer comprising a polarized carbon-based nano material, disposed between the first electrode and the second electrode, the channel forming layer being configured to form a channel based on a field between the first electrode and the second electrode; and
 a sensing layer disposed on the channel forming layer, comprising a medium material, the sensing layer being configured to sense, in a predetermined period of time, a concentration of glucose permanently bonded by an oxidant to a medium material,
 a hexagonal-boron nitride (h-BN) layer disposed between the channel forming layer and the protecting layer, wherein a side surface of the h-Bn layer directly contacts a side surface of the first electrode, another side surface of the h-Bn layer directly contacts a side surface of the second electrode, and a top surface of the h-BN layer directly contacts the channel forming layer,
 wherein the respective bottom surfaces of the first electrode, the second electrode, and the h-BN layer are disposed on top of, and directly contact, a surface of the protecting layer,
 wherein the concentration of glucose is measured based on an S parameter value and an RLGC value obtained as a result of a high frequency electrical signal being applied to the first electrode and the second electrode.

2. The apparatus of claim 1, wherein the protecting layer is on the substrate and comprises a high-resistance silicon oxide based material.

3. The apparatus of claim 1, wherein the polarized carbon-based nano material is polarized along a direction of the field.

4. The apparatus of claim 1, wherein, in response to the field being formed by applying direct current (DC) voltage or alternating current (AC) voltage to the first electrode and the second electrode, the channel forming layer is further configured to form the channel in the channel forming layer, based on a dielectric phoresis scheme.

5. The apparatus of claim 1, wherein the channel forming layer comprises a dipole moment that causes the polarized carbon-based nano material to migrate toward the field.

6. The apparatus of claim 1, wherein the polarized carbon-based nano material comprises a layer of graphene or carbon nano tube (CNT).

7. The apparatus of claim 1, wherein the medium material comprises poly aminophenyl boronic acid.

8. The apparatus of claim 1,
wherein the h-BN layer is configured to decrease a dielectric loss of electrons within a range of the applied radio frequency signal.

9. The apparatus of claim 1,
wherein the sensing apparatus is configured to permanently bond glucose by an oxidant to a medium material, while measuring a concentration of glucose based on inductance values, at medium material concentrations of 1 mM to 5 mM;
wherein a first parameter, measured in units of dB, corresponds to an amount of electrons that are reflected and returned to an electrode, when electrons migrate through the channel between the electrode and an opposite electrode; and
wherein a second parameter, measured in units of dB, corresponds to an amount of electrons that migrate through the channel, thereby moving from the electrode to the opposite electrode.

10. The apparatus of claim 1, wherein a left-side surface of the h-Bn layer directly contacts a right-side surface of the first electrode, a right-side surface of the h-Bn layer directly contacts a left-side surface of the second electrode, and a bottom surface of the h-Bn layer is aligned with a bottom surface of the first electrode and a bottom surface of the second electrode.

* * * * *